United States Patent
Nakasone et al.

(10) Patent No.: US 9,678,035 B2
(45) Date of Patent: Jun. 13, 2017

(54) HYDROCARBON GAS SENSOR

(71) Applicant: NGK Insulators, Ltd., Nagoya-Shi (JP)

(72) Inventors: Osamu Nakasone, Inabe (JP); Satoshi Nishikawa, Chita (JP); Shotarou Niizuma, Kasugai (JP); Noriko Hirata, Nagoya (JP); Yuki Nakayama, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 483 days.

(21) Appl. No.: 14/274,994

(22) Filed: May 12, 2014

(65) Prior Publication Data

US 2014/0332378 A1    Nov. 13, 2014

(30) Foreign Application Priority Data

May 13, 2013  (JP) .................................. 2013-101003

(51) Int. Cl.
  *C25B 11/12* (2006.01)
  *G01N 7/00* (2006.01)
  (Continued)

(52) U.S. Cl.
  CPC ......... *G01N 27/41* (2013.01); *G01N 27/4074* (2013.01); *G01N 27/419* (2013.01); *G01N 33/0047* (2013.01)

(58) Field of Classification Search
  CPC .......... C25B 11/12; G01N 7/00; G01N 21/00; G01N 27/00; G01N 31/00; G01N 33/00; G01N 25/18; G01N 1/22
  (Continued)

(56) References Cited

U.S. PATENT DOCUMENTS 5,879,525 A    3/1999 Kato
5,893,968 A    4/1999 Kato
(Continued)

FOREIGN PATENT DOCUMENTS

EP    0 731 351 A2    9/1996
EP    0 849 590 A2    6/1998
(Continued)

OTHER PUBLICATIONS

Extended European Search Report (Application No. 14167743.5) dated Nov. 4, 2014.
U.S. Appl. No. 14/275,048, filed May 12, 2014, Nakasone, et al.

*Primary Examiner* — Brian J Sines
(74) *Attorney, Agent, or Firm* — Burr & Brown, PLLC (57) ABSTRACT

Provided is a gas sensor capable of accurately obtaining a hydrocarbon gas concentration even if a measurement gas contains water vapor. A main pumping cell adjusts an oxygen partial pressure of a first internal space such that a hydrocarbon gas in a measurement gas is not substantially burned in the first internal space. An auxiliary pumping cell adjusts an oxygen partial pressure of a second internal space such that inflammable gas components except for hydrocarbon are selectively burned. Then, a measuring pumping cell supplies oxygen to a surface of a measuring electrode. As a result, hydrocarbon existing in the measurement gas being in contact with the measuring electrode is all burned on the surface of the measuring electrode and, based on the magnitude of a current flowing between the measuring electrode and a main pumping electrode at that time, identifies a concentration of a hydrocarbon gas component existing in the measurement gas.

19 Claims, 3 Drawing Sheets (51) Int. Cl.
  *G01N 21/00*   (2006.01)
  *G01N 27/00*   (2006.01)
  *G01N 27/41*   (2006.01)
  *G01N 27/407*  (2006.01)
  *G01N 27/419*  (2006.01)
  *G01N 33/00*   (2006.01)

(58) Field of Classification Search
  USPC ........... 204/294; 422/83, 90, 93, 98; 436/43, 436/139, 140, 141, 142, 143, 149, 181
  See application file for complete search history.

(56) References Cited

U.S. PATENT DOCUMENTS

| | | | |
|---|---|---|---|
| 5,902,469 A * | 5/1999 | Kato et al. | 204/425 |
| 5,985,118 A * | 11/1999 | Makino et al. | 204/426 |
| 6,344,119 B2 * | 2/2002 | Kato et al. | 204/425 |
| 2001/0008211 A1 * | 7/2001 | Kato et al. | 204/426 |
| 2003/0121801 A1 * | 7/2003 | Inaba et al. | 205/785.5 |
| 2005/0235631 A1 * | 10/2005 | Schumann | 60/276 |
| 2011/0240487 A1 * | 10/2011 | Ishikawa et al. | 205/781 |
| 2013/0260983 A1 * | 10/2013 | Omori et al. | 501/134 |

FOREIGN PATENT DOCUMENTS

| | | |
|---|---|---|
| EP | 0 867 715 A1 | 9/1998 |
| EP | 0 887 640 A1 | 12/1998 |
| EP | 1 912 064 A1 | 4/2008 |
| EP | 2 312 307 A1 | 4/2011 |
| EP | 2 369 331 A1 | 9/2011 |
| JP | 3450084 B2 | 9/2003 |

* cited by examiner

HYDROCARBON GAS SENSOR

BACKGROUND OF THE INVENTION

Field of the Invention

The present invention relates to a hydrocarbon gas sensor that detects a hydrocarbon gas in a measurement gas.

Description of Related Art

There has been already known an apparatus capable of measuring a total concentration of inflammable gases in a measurement gas containing, as inflammable gases, carbon monoxide (CO), hydrogen ($H_2$), and hydrocarbon (HC) such as propane ($C_3H_8$), or the concentration of a hydrocarbon gas in the inflammable gases (for example, see Japanese Patent Publication No. 3450084). Combustion exhaust gases in, for example, an internal combustion engine, an external combustion engine, and a combustion path are illustrated as examples of the measurement gases.

In outline, the apparatus disclosed in Japanese Patent Publication No. 3450084 is mainly composed of zirconia being an oxygen-ion conductive solid electrolyte and includes a first processing zone and a second processing zone each defined from the outside. This apparatus is configured to apply, between an opening portion facing the outside and the first processing zone and between the first processing zone and the second processing zone, a predetermined diffusion resistance to a gas atmosphere flowing therebetween. In this apparatus, the measurement gas containing inflammable gas components is first guided to the first processing zone from the outside of the apparatus with a predetermined diffusion resistance, and then, its oxygen partial pressure is reduced such that the inflammable gas components are not substantially burned, through an oxygen pumping action by a first electrochemical oxygen pumping cell in the first processing zone. After that, the measurement gas is guided to the second processing zone with a predetermined diffusion resistance. Then, in the second processing zone, the inflammable gas components existing in the atmosphere are burned when being supplied with oxygen through the oxygen pumping action by a second electrochemical oxygen pumping cell. The pump current flowing through the second electrochemical oxygen pumping cell or the voltage generated between the electrodes of the second electrochemical oxygen pumping cell is detected in this burning, to thereby obtain a concentration of the inflammable gas in the measurement gas based on the detected value.

A selective oxidation catalyst, which does not oxidize a hydrocarbon gas but selectively oxides inflammable gases except for hydrocarbon gases, such as a carbon monoxide gas and a hydrogen gas, is placed between the opening portion and the first processing zone, so that the hydrocarbon gas alone is guided to the second processing zone As a result, the concentration of the hydrocarbon gas can be obtained.

The above-mentioned concentration measurement technique with the apparatus disclosed in Japanese Patent Publication No. 3450084 is capable of obtaining a desired concentration with high accuracy in case where the measurement gas contains no water vapor (for example, in a case of a binary system of oxygen and inflammable gas).

Actually assumed as the measurement gas in the above-mentioned concentration measurement method is, however, a combustion exhaust gas mainly in an internal combustion engine, external combustion engine, or combustion path. Such a combustion exhaust gas contains approximately 2% to 12% (at a volume percentage) of water vapor generated through burning of the inflammable gas.

If the above-mentioned technique is applied to a measurement gas containing not only oxygen and inflammable gas but also water vapor to control the oxygen partial pressure to such a small value as not to substantially burn the inflammable gas in the first processing zone, the water vapor is decomposed, generating a hydrogen gas being an inflammable gas. The generated hydrogen gas flows into the second processing zone together with the inflammable gas that is originally a measurement target, which has been contained in the measurement gas, and is then burned in the second processing zone. In other words, a larger amount of oxygen than required for burning the inflammable gas being an original measurement target is consumed, resulting in a large error in the concentration value obtained. For example, for the oxygen partial pressure of $10^{-14}$ atm to $10^{-20}$ atm in the first processing zone, the concentration of the hydrogen gas to be generated through decomposition of water vapor may reach several %.

Japanese Patent Publication No. 3450084 also discloses the configuration in which hydrogen in the measurement gas is pumped out by a proton pump provided, and then, the measurement gas is guided to the second electrochemical pumping cell. In this configuration, however, a solid electrolyte formed of a material different from zirconia is used for only the proton pump, resulting in a complex process. Also, the complex configuration is disadvantageous in costs.

SUMMARY OF THE INVENTION

The present invention is directed to a hydrocarbon gas sensor that detects a hydrocarbon gas in a measurement gas.

According to the present invention, a hydrocarbon gas sensor has a sensor element formed of an oxygen-ion conductive solid electrolyte and identifies a concentration of a hydrocarbon gas component of a measurement gas based on a current flowing through the solid electrolyte when the hydrocarbon gas component is burned, and the hydrocarbon gas sensor includes: a first diffusion control part that is in communication with the outside and applies a first diffusion resistance to the measurement gas; a first internal space that is in communication with the first diffusion control part, into which a measurement gas is introduced with the first diffusion resistance from the outside; a second diffusion control part that is in communication with the first internal space and applies a second diffusion resistance to the measurement gas; a second internal space that is in communication with the second diffusion control part, into which a measurement gas is introduced with the second diffusion resistance from the first internal space; a third diffusion control part that applies a third diffusion resistance to the measurement gas introduced into the second internal space; a first electrochemical pumping cell formed of a first internal electrode formed to face the first internal space, a first external electrode formed on an outer surface of the sensor element, and the solid electrolyte located between the first internal electrode and the first external electrode; a second electrochemical pumping cell formed of a second internal electrode formed to face the second internal space, a second external electrode formed on the outer surface of the sensor element, and the solid electrolyte located between the second internal electrode and the second external electrode; a measuring pumping cell formed of a measuring electrode, a third external electrode, and the solid electrolyte located between the measuring electrode and the third external electrode, the measuring electrode being formed so as to come into contact with the measurement gas to which the third diffusion resistance has been applied, the third external electrode being formed on the outer surface of the sensor element; a reference gas space into which a reference gas is introduced; and a reference electrode formed to face the reference gas space. The first electrochemical pumping cell adjusts an oxygen partial pressure of the first internal space such that a hydrocarbon gas in the measurement gas is not substantially burned in the first internal space. The second electrochemical pumping cell adjusts an oxygen partial pressure of the second internal space such that non-target inflammable gas components of inflammable gas components existing in the second internal space are selectively burned, the non-target inflammable gas components being inflammable gas components including at least hydrogen or carbon monoxide and excluding the hydrocarbon. The hydrocarbon gas sensor burns, on a surface of the measuring electrode, all of the hydrocarbon existing in the measurement gas in contact with the measuring electrode after burning of the non-target inflammable gas components, by supplying oxygen to the surface of the measuring electrode by the measuring pumping cell, to thereby identify the concentration of the hydrocarbon gas component existing in the measurement gas based on the magnitude of a current flowing between the measuring electrode and the third external electrode or between the measuring electrode and the reference electrode.

According to the present invention, a hydrocarbon gas concentration can be obtained accurately without being affected by water vapor or/and carbon dioxide even if a measurement gas contains water vapor or/and carbon dioxide in addition to an inflammable component except for hydrocarbon.

An object of the present invention is therefore to provide a hydrocarbon gas sensor capable of accurately obtaining a concentration of a hydrocarbon gas in a measurement gas containing a carbon monoxide gas, a hydrogen gas, and a hydrocarbon gas as inflammable gases and further containing water vapor or/and carbon dioxide.

DETAILED DESCRIPTION OF THE INVENTION

First Embodiment

Outline Configuration of Gas Sensor

Figure 1:
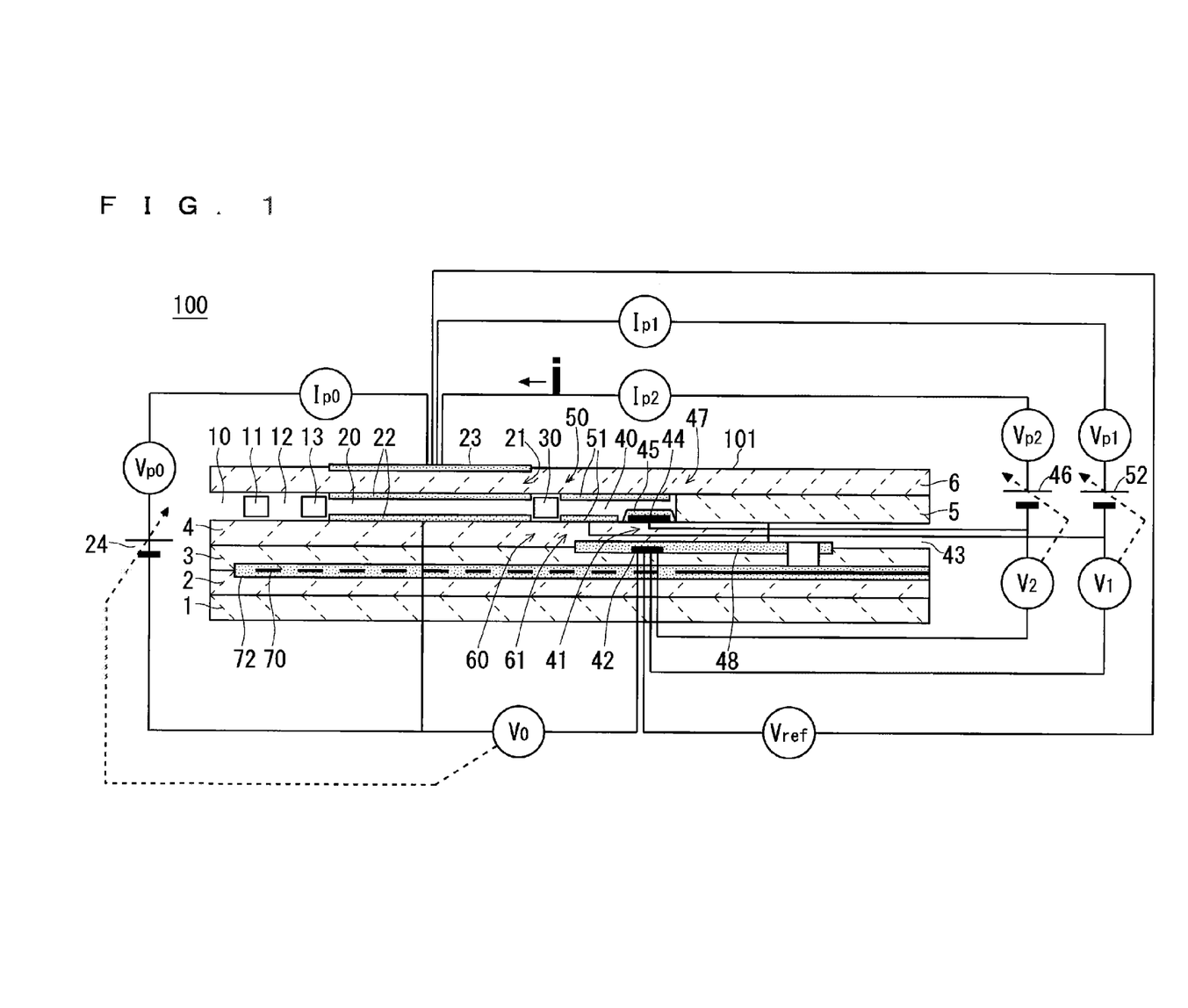
FIG. 1 is a cross-sectional view schematically showing the structure of a gas sensor 100 according to a first embodiment.

FIG. 1 is a cross-sectional view schematically showing the structure of a gas sensor 100 according to a first embodiment of the present invention. The gas sensor 100 according to this embodiment serves to detect various hydrocarbon (HC) gases such as ethylene ($C_2H_4$), propane ($C_3H_8$), and propylene ($C_3H_6$) and obtain a concentration thereof. A sensor element 101 being a main part of the gas sensor 100 includes, as a structural material, ceramics mainly composed of zirconia that is an oxygen-ion conductive solid electrolyte.

Specifically, the sensor element 101 has the structure in which six layers, namely, a first substrate layer 1, a second substrate layer 2, a third substrate layer 3, a first solid electrolyte layer 4, a spacer layer 5, and a second solid electrolyte layer 6 each formed of an oxygen-ion conductive solid electrolyte, are laminated in the stated order from the bottom side of the sheet of FIG. 1.

Provided between a lower surface of the second solid electrolyte layer 6 and an upper surface of the first solid electrolyte layer 4 on one-end-portion side of the sensor element 101 are a gas inlet 10, a first diffusion control part 11, a first internal space 20, a second diffusion control part 30, and a second internal space 40. A buffer space 12 and a fourth diffusion control part 13 may be further provided between the first diffusion control part 11 and the first internal space 20. The gas inlet 10, the first diffusion control part 11, the buffer space 12, the fourth diffusion control part 13, the first internal space 20, the second diffusion control part 30, and the second internal space 40 are adjacently formed so as to be in communication with one another in the stated order. The part extending from the gas inlet 10 to the second internal space 40 is referred to as a gas distribution part as well.

The gas inlet 10, the buffer space 12, the first internal space 20, and the second internal space 40 are interior spaces provided by hollowing out the spacer layer 5. The buffer space 12, the first internal space 20, and the second internal space 40 are each provided, with its upper portion defined by the lower surface of the second solid electrolyte layer 6, its lower portion defined by the upper surface of the first solid electrolyte layer 4, and its side portion defined by a side surface of the spacer layer 5.

The first diffusion control part 11, the second diffusion control part 30, and the fourth diffusion control part 13 are each provided as two horizontally long slits (which are openings longitudinally extending to be vertical to the sheet of FIG. 1).

At a position that is located between an upper surface of the third substrate layer 3 and a lower surface of the spacer layer 5 and is farther from the distal-end side than the gas distribution part, a reference gas introduction space 43 is provided. The reference gas introduction space 43 is an interior space with its upper portion defined by the lower surface of the spacer layer 5, its lower portion defined by the upper surface of the third substrate layer 3, and its side portion defined by a side surface of the first solid electrolyte layer 4. For example, oxygen or air is introduced into the reference gas introduction space 43 as a reference gas.

The gas inlet 10 is a part being open to the outside. Through this gas inlet 10, a measurement gas is taken into the sensor element 101 from the outside.

The first diffusion control part 11 is a part that applies a predetermined diffusion resistance to the measurement gas taken through the gas inlet 10.

The buffer space 12 is provided to cancel concentration fluctuations of the measurement gas which are caused due to pressure fluctuations of the measurement gas in the outside (in a case where the measurement gas is an automobile exhaust gas, pulsations of the exhaust gas pressure). The sensor element 101 does not necessarily need to include the buffer space 12.

The fourth diffusion control part 13 is a part that applies a predetermined diffusion resistance to the measurement gas introduced from the buffer space 12 into the first internal space 20. The fourth diffusion control part 13 is a part provided in association with the provision of the buffer space 12.

The first diffusion control part 11 and the first internal space 20 are directly in communication with each other if the buffer space 12 and the fourth diffusion control part 13 are not provided.

The first internal space 20 is provided as a space for adjusting an oxygen partial pressure of the measurement gas introduced through the gas inlet 10. This oxygen partial pressure is adjusted through the operation of a main pumping cell 21.

The main pumping cell 21 is an electrochemical pumping cell (first electrochemical pumping cell) formed of an inside pump electrode 22, an outside pump electrode 23, and the oxygen-ion conductive solid electrolyte sandwiched between these electrodes. The inside pump electrode 22 is provided on substantially the entire upper surface of the first solid electrolyte layer 4, substantially the entire lower surface of the second solid electrolyte layer 6, and substantially the entire side surface of the spacer layer 5, those surfaces defining the first internal space 20. The outside pump electrode 23 is provided so as to be exposed to the outside in the region corresponding to the inside pump electrode 22 on the upper surface of the second solid electrolyte layer 6. The inside pump electrode 22 and the outside pump electrode 23 are each formed as a porous cermet electrode rectangular in plan view (for example, a cermet electrode made of a precious metal such as Pt containing 0.1 wt % to 30.0 wt % of Au, and $ZrO_2$).

The main pumping cell 21 causes, upon application of a pump voltage Vp0 by a variable power source 24 provided outside the sensor element 101, a pump current Ip0 to flow between the outside pump electrode 23 and the inside pump electrode 22, allowing oxygen in the first internal space 20 to be pumped out to the outside or outside oxygen to be pumped into the first internal space 20.

In the sensor element 101, the inside pump electrode 22, a reference electrode 42 sandwiched between the upper surface of the third substrate layer 3 and the first solid electrolyte layer 4, and the oxygen-ion conductive solid electrolyte sandwiched between these electrodes constitute a first oxygen-partial-pressure detection sensor cell 60 being an electrochemical sensor cell. The reference electrode 42 is an electrode substantially rectangular in plan view, which is formed of a porous cermet similar to, for example, the outside pump electrode. Provided around the reference electrode 42 is a reference gas introduction layer 48 that is made of porous alumina and is continuous with the reference gas introduction space, so that the reference gas of the reference gas introduction space 43 is introduced to the surface of the reference electrode 42. In the first oxygen-partial-pressure detection sensor cell 60, an electromotive force V0 is generated between the inside pump electrode 22 and the reference electrode 42, which results from an oxygen concentration difference between the atmosphere in the first internal space 20 and the reference gas of the reference gas introduction space 43.

The electromotive force V0 generated in the first oxygen-partial-pressure detection sensor cell 60 varies in accordance with the oxygen partial pressure in the atmosphere existing in the first internal space 20. The sensor element 101 uses this electromotive force V0 to feedback-control the variable power source 24 for the main pumping cell 21. This allows the pump voltage Vp0, which is applied to the main pumping cell 21 by the variable power source 24, to be controlled in accordance with the oxygen partial pressure in the atmosphere of the first internal space 20.

The second diffusion control part 30 is a part that applies a predetermined diffusion resistance to the measurement gas introduced from the first internal space 20 into the second internal space 40.

The second internal space 40 is provided as a space for performing the process for measuring a concentration of the hydrocarbon gas in the measurement gas introduced through the second diffusion control part 30. In the second internal space 40, oxygen can be supplied from the outside through the operation of an auxiliary pumping cell 50.

The auxiliary pumping cell 50 is an auxiliary electrochemical pumping cell (second electrochemical pumping cell) formed of an auxiliary pump electrode 51, the outside pump electrode 23, and the oxygen-ion conductive solid electrolyte sandwiched between these electrodes. The auxiliary pump electrode 51 is provided on substantially the entire upper surface of the first solid electrolyte layer 4, the lower surface of the second solid electrolyte layer 6, and part of the side surface of the spacer layer 5, those surfaces defining the second internal space 40. The auxiliary pump electrode 51 is formed as a porous cermet electrode rectangular in plan view, similarly to the outside pump electrode 23 and the inside pump electrode 22. The use of the outside pump electrode 23 is not necessarily required, and other cermet electrode provided on the outer surface of the sensor element 101 may form the auxiliary pumping cell 50, in place of the outside pump electrode 23.

The auxiliary pumping cell 50 causes, upon application of a pump voltage Vp1 by a variable power source 52 provided outside the sensor element 101, a pump current Ip1 to flow between the outside pump electrode 23 and the auxiliary pump electrode 51, so that oxygen can be pumped into the second internal space 40.

In the sensor element 101, the auxiliary pump electrode 51, the reference electrode 42, and the oxygen-ion conductive solid electrolyte sandwiched between these electrodes constitute a second oxygen-partial-pressure detection sensor cell 61 being an electrochemical sensor cell. In the second oxygen-partial-pressure detection sensor cell 61, an electromotive force V1 is generated between the auxiliary pump electrode 51 and the reference electrode 42, which results from an oxygen concentration difference between the atmosphere in the second internal space 40 and the reference gas of the reference gas introduction space 43.

The electromotive force V1 to be generated in the second oxygen-partial-pressure detection sensor cell 61 varies in accordance with the oxygen partial pressure in the atmosphere existing in the second internal space 40. The sensor element 101 uses this electromotive force V1 to feedback-control the variable power source 52 for the auxiliary pumping cell 50. This allows the pump voltage Vp1, which is applied to the auxiliary pumping cell 50 by the variable power source 52, to be controlled in accordance with the oxygen partial pressure in the atmosphere of the second internal space 40.

The sensor element 101 further includes a measuring sensor cell 41 and a measuring pumping cell 47. The measuring sensor cell 41 is an electrochemical sensor cell formed of the measuring electrode 44, the reference electrode 42, and the oxygen-ion conductive solid electrolyte sandwiched between these electrodes. The measuring pumping cell 47 is an electrochemical pumping cell formed of the outside pump electrode 23, the measuring electrode 44, and the oxygen-ion conductive solid electrolyte sandwiched between these electrodes.

The measuring electrode 44 is an electrode substantially rectangular in plan view, which is formed of a porous cermet similarly to, for example, the outside pump electrode. However, the measuring electrode 44 is covered with a third diffusion control part 45. The third diffusion control part 45 is a porous alumina layer, which is a part that applies a predetermined diffusion resistance to the measurement gas expected to come into contact with the measuring electrode 44 in the second internal space 40. In other words, the third diffusion control part 45, which can be assumed as a layer provided to limit an amount of the inflammable gas that comes into contact with the measuring electrode 44, isolates the measuring electrode 44 from the second internal space 40. The third diffusion control part 45 also functions as an electrode protecting layer that protects the measuring electrode 44 from, for example, particle adhesion.

In the measuring sensor cell 41, an electromotive force V2 is generated between the measuring electrode 44 and the reference electrode 42, which results from an oxygen concentration difference between the atmosphere in the vicinity of the surface of the measuring electrode 44 covered with the third diffusion control part 45 and the reference gas of the reference gas introduction space 43. In this embodiment, the surface of the measuring electrode 44 also includes wall portions of a number of minute holes located to be in communication with the outside in the porous cermet forming the measuring electrode 44, not only the portion being in contact with the third diffusion control part 45.

The electromotive force V2 to be generated in the measuring sensor cell 41 varies in accordance with an oxygen partial pressure of the atmosphere existing in the vicinity of the surface of the measuring electrode 44. The sensor element 101 uses this electromotive force V2 to feedback-control a variable power source 46 for the measuring pumping cell 47. This allows the pump voltage Vp2, which is applied to the measuring pumping cell 47 by the variable power source 46, to be controlled in accordance with the oxygen partial pressure of the atmosphere in the vicinity of the surface of the measuring electrode 44.

The sensor element 101 is configured to measure an electromotive force $V_{ref}$ generated between the outside pump electrode 23 and the reference electrode 42 to obtain the oxygen partial pressure outside the sensor element 101.

In the sensor element 101, further, a heater 70 is formed to be vertically sandwiched between the second substrate layer 2 and the third substrate layer 3. The heater 70 generates heat by power feeding from the outside through a heater electrode (not shown) provided on the lower surface of the first substrate layer 1. Heat generation by the heater 70 increases the oxygen-ion conductivity of the solid electrolyte forming the sensor element 101. The heater 70 is buried over the entire area extending from the first internal space 20 to the second internal space 40 to heat a predetermined portion of the sensor element 101 to a predetermined temperature or maintain the temperature of the predetermined portion at a predetermined temperature. Formed on the upper and lower surfaces of the heater 70 is a heater insulating layer 72 made of, for example, alumina to obtain electrical insulation between the second substrate layer 2 and the third substrate layer 3 (hereinafter, the heater 70, the heater electrode, and the heater insulating layer 72 are correctively referred to as a heater part as well).

Measurement of Hydrocarbon Gas Concentration

The technique of identifying a hydrocarbon gas concentration with the gas sensor 100 having the above-mentioned configuration will be described next.

First, the sensor element 101 is placed in the atmosphere of the measurement gas containing a hydrocarbon gas and carbon monoxide, hydrogen, and the like, as inflammable gases, and also containing oxygen, water vapor ($H_2O$), carbon dioxide, noninflammable gases, and the like. So, the measurement gas is introduced into the sensor element 101 through the gas inlet 10. The measurement gas which has been introduced into the sensor element 101 reaches the first internal space 20, following the application of a predetermined diffusion resistance by the first diffusion control part 11 or further by the fourth diffusion control part 13.

In the first internal space 20, through the operation of the main pumping cell 21, oxygen is pumped out such that the oxygen partial pressure of the inside measurement gas has a sufficiently low predetermined value (for example, $10^{-14}$ atm to $10^{-20}$ atm) to an extent that the inflammable gas contained in the measurement gas does not burn, at least, to an extent that the hydrocarbon gas contained in the measurement gas does not substantially burn. Here, "the hydrocarbon gas contained in the measurement gas does not substantially burn" means that most of the hydrocarbon gas introduced into the first internal space 20 is introduced into the second internal space 40.

Actual pumping-out of oxygen is implemented in a manner that a target value of the electromotive force V0, which is generated between the inside pump electrode 22 and the reference electrode 42 in the first oxygen-partial-pressure detection sensor cell 60, is preliminarily determined to such a predetermined value as to obtain the above-mentioned oxygen partial pressure, then the variable power source 24 controls the pump voltage Vp0 to be applied to the main pumping cell 21 in accordance with a difference between a value of the actual electromotive force V0 and the target value. For example, when the measurement gas containing a large amount of oxygen reaches the first internal space 20, the value of the electromotive force V0 varies considerably from the target value. Therefore, the variable power source 24 controls the pump voltage Vp0 to be applied to the main pumping cell 21 in order to reduce such a variation.

The target value of the electromotive force V0 is preferably set such that a (target) oxygen partial pressure in the first internal space 20 becomes smaller as the oxygen partial pressure in the measurement gas that has reached the first internal space 20 becomes larger (as a difference between the measured value of the electromotive force V0 and the latest determined target value becomes larger). This allows oxygen to be pumped out more reliably.

The measurement gas which has an oxygen partial pressure decreased as described above reaches the second internal space 40, following the application of a predetermined diffusion resistance by the second diffusion control part 30.

Under the condition that the measurement gas contains water vapor, however, the decomposition reaction of water vapor ($2H_2O \rightarrow 2H_2 + O_2$) is promoted in the first internal space 20 to generate hydrogen and oxygen, as a result of the above-mentioned pumping-out of oxygen from the first internal space 20. Of those, oxygen is pumped out by the main pumping cell 21, but hydrogen is introduced into the second internal space together with the measurement gas.

Similarly, under the condition that the measurement gas contains carbon dioxide, the decomposition reaction of carbon dioxide ($2CO_2 \rightarrow 2CO + O_2$) is promoted in the first internal space 20 to generate carbon monoxide and oxygen, as a result of the above-mentioned pumping-out of oxygen from the first internal space 20. Of those, oxygen is pumped out by the main pumping cell 21, but carbon monoxide is introduced into the second internal space 40 together with the measurement gas.

In the second internal space 40, pumping-in of oxygen is performed through the operation of the auxiliary pumping cell 50. This pumping-in of oxygen is performed to cause, among the inflammable gases contained in the measurement gas that has reached the second internal space 40 (containing hydrogen or/and carbon monoxide generated in the first internal space 20), non-target inflammable gas components to selectively react with the inside oxygen at a time when the measurement gas reaches the second internal space 40. The non-target inflammable gas components include at least hydrogen or carbon monoxide and exclude a hydrocarbon gas. For example, in the case of hydrogen, oxygen is pumped into the second internal space 40 to promote the reaction of $2H_2+O_2 \rightarrow 2H_2O$ for hydrogen and promote the reaction of $2CO+O_2 \rightarrow 2CO_2$ for carbon monoxide.

Actual pumping-in of oxygen is implemented in a manner that a target value of the electromotive force V1 which is generated between the auxiliary pump electrode 51 and the reference electrode 42 in the second oxygen-partial-pressure detection sensor cell 61, is preliminarily determined to such a predetermined value as to obtain an oxygen partial pressure for providing an oxygen concentration large enough to burn non-target inflammable gas components in the above-mentioned manner, then the variable power source 52 controls the pump voltage Vp1 to be applied to the auxiliary pumping cell 50 in accordance with a difference between a value of the actual electromotive force V0 and the target value. For example, when the measurement gas containing a large amount of inflammable gases reaches the second internal space 40 and reacts with oxygen, an oxygen partial pressure decreases, which causes the value of the electromotive force V1 to vary considerably from the target value. Therefore, the variable power source 52 controls the pump voltage Vp1 to be applied to the auxiliary pumping cell 50 so as to decrease the above-mentioned variations.

The control made in this manner allows, among the inflammable gas components, hydrogen and carbon monoxide being non-target inflammable gas components to be selectively burned with ease and a hydrocarbon gas to be hardly burned in the second internal space 40. This is because hydrogen and carbon monoxide have gas diffusion rates larger than the gas diffusion rate of a hydrocarbon gas and thus come into contact with oxygen, which is to be pumped, and then are burned in prior to the hydrocarbon gas, and because hydrogen and carbon monoxide are more likely to combine with oxygen, namely, are more likely to burn, than a hydrocarbon gas.

The measurement gas whose non-target inflammable gas components have been burned reaches the surface of the measuring electrode 44, following the application of a predetermined diffusion resistance by the third diffusion control part 45.

At the surface of the measuring electrode 44, pumping-in of oxygen is performed through the operation of the measuring pumping cell 47. This pumping-in of oxygen is performed so as to reliably burn the hydrocarbon gas contained in the measurement gas that has reached near the surface of the measuring electrode 44.

Actual pumping-in of oxygen is implemented in a manner that a target value of the electromotive force V2, which is generated between the measuring electrode 44 and the reference electrode 42 in the measuring sensor cell 41, is preliminarily determined to such a predetermined value as to obtain an oxygen partial pressure for providing an oxygen concentration large enough to burn a hydrocarbon gas, then the variable power source 46 controls the pump voltage Vp2 to be applied to the measuring pumping cell 47 in accordance with a difference between the actual value of the electromotive force V2 and the target value. For example, when the measurement gas containing a large amount of hydrocarbon gases reaches near the surface of the measuring electrode 44 and reacts with oxygen, an oxygen partial pressure decreases, which causes the value of the electromotive force V2 to vary largely from the target value. Therefore, the variable power source 46 controls the pump voltage Vp2 to be applied to the measuring pumping cell 47 so as to decrease the above-mentioned variations.

Figure 2:
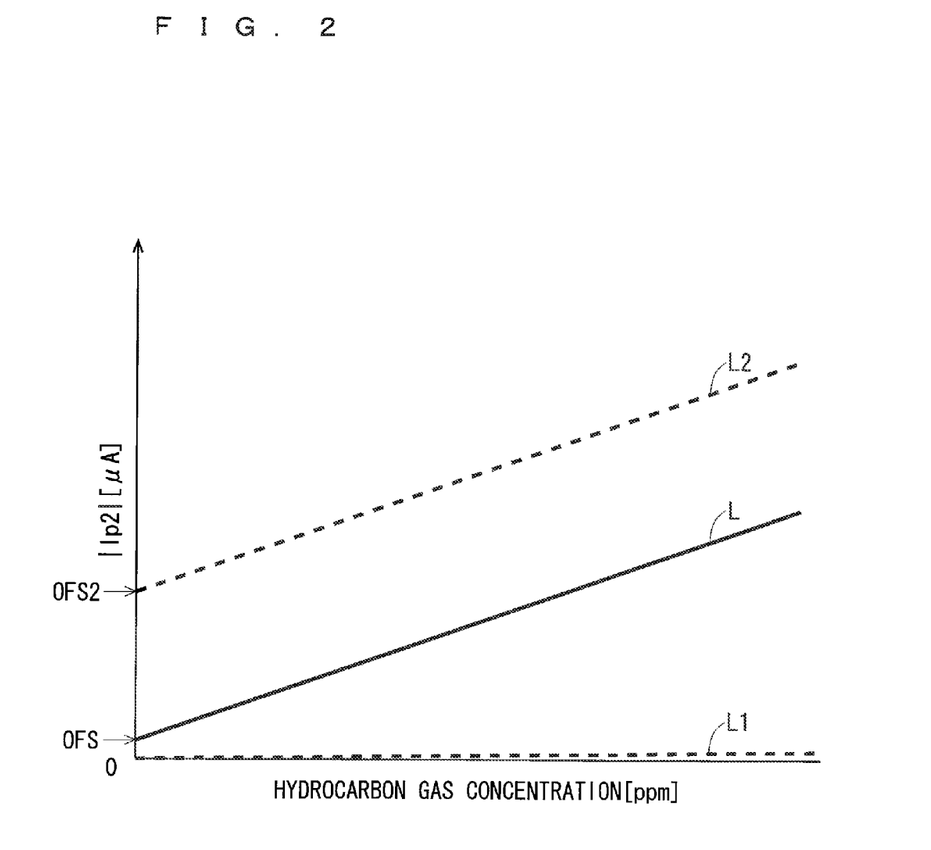
FIG. 2 illustrates a graph (sensitivity characteristics) showing a functional relationship between an absolute value of a HC detection current Ip2 and an actual hydrocarbon gas concentration.

The current Ip2 flowing through the measuring pumping cell 47 at this time (HC detection current) is substantially proportional to the HC concentration of the measurement gas (the HC detection current Ip2 and the HC concentration have a linear relationship, see FIG. 2). Thus, the gas sensor 100 according to this embodiment detects this HC detection current Ip2 and, based on the detected value, obtains the HC gas concentration of the measurement gas.

FIG. 2 illustrates a graph (sensitivity characteristics) showing a functional relationship between an absolute value of the HC detection current Ip2 and an actual hydrocarbon gas concentration. FIG. 2 shows a HC detection current value as an absolute value for brevity of the description. More specifically, in a case where oxygen is pumped in to the surface of the measuring electrode 44 in the gas sensor 100 of FIG. 1, the HC detection current Ip2 has a negative value.

FIG. 2 illustrates an ideal functional relationship between the HC detection current Ip2 and the hydrocarbon gas concentration by the solid line L. The solid line L is a straight line with a non-zero intercept on the vertical axis. Although the value of the HC detection current Ip2 with zero hydrocarbon gas concentration (with no hydrocarbon gas) should be zero, in actuality, a slight amount of the pump-in current for obtaining a target oxygen concentration, namely, a slight amount of the HC detection current Ip2 flows, even when no hydrocarbon gas exists. This is because oxygen becomes scarce compared to a target oxygen concentration in the vicinity of the surface of the measuring electrode 44, due to an influence of the main pumping cell 21 pumping out oxygen. In particular, the HC detection current Ip2 at this time is referred to as an offset current OFS.

In the gas sensor 100 according to this embodiment, prior to its use, the sensitivity characteristics (specifically, the offset current OFS and the inclination of the graph) as shown in FIG. 2 are preliminarily identified for each sensor element 101 based on the value of the BC detection current Ip2 obtained when the gas having a known hydrocarbon gas concentration is supplied to the gas sensor 100. In actually detecting a hydrocarbon gas, the Ip2 value is constantly measured, to thereby obtain a hydrocarbon gas concentration corresponding to each individual measured value based on the sensitivity characteristics preliminarily identified.

For accurate measurement of a hydrocarbon gas concentration in this manner, it is necessary to avoid reaction between an inflammable gas and oxygen in the first internal space and to burn only non-target inflammable gas components being the inflammable gases other than a hydrocarbon gas without burning the hydrocarbon gas in the second internal space.

To satisfy those needs, the target values of the electromotive force V0 in the first oxygen-partial-pressure detection sensor cell 59, the electromotive force V1 in the second oxygen-partial-pressure detection sensor cell 61, and the electromotive force V2 in the measuring sensor cell 41 are preferably determined so as to satisfy such a relationship that the oxygen partial pressure of the second internal space 40 is larger than the oxygen partial pressure of the first internal space 20 and that the oxygen partial pressure in the vicinity of the surface of the measuring electrode 44 is larger than the oxygen partial pressure of the second internal space 40.

If a little amount of oxygen is pumped out due to an excessively large oxygen partial pressure in the first internal space 20 or if even the hydrocarbon gas is oxidized before reaching the measuring electrode 44 due to an excessively large oxygen partial pressure in the second internal space 40, the sensitivity characteristics as indicated by the broken line L1 with a small inclination, shown in FIG. 2, are obtained. In such a case, there is little dependence of Ip2 on the hydrocarbon gas concentration, making it difficult to accurately obtain a hydrocarbon gas concentration based on the Ip2 value.

If the oxygen partial pressure in the second internal space 40 is excessively small, meanwhile, the non-target inflammable gas components in the second internal space 40 burn insufficiently. This causes even the non-target inflammable gas components to reach the measuring electrode 44, resulting in sensitivity characteristics in which the value of the offset current OFS2 is large as indicated by the broken line L2 in FIG. 2. In such a case, the non-target inflammable gas components including hydrogen or/and carbon monoxide generated in the first internal space 20 and excluding a hydrocarbon gas are burned with oxygen pumped in from the measuring electrode 44, irrespective of the presence or absence of a hydrocarbon gas in the measurement gas. Thus, the sensitivity characteristics cannot be identified correctly because the sensitivity characteristics cannot be determined correctly due to an excessively increased ratio of the offset current OFS2 to the value of the HC detection current Ip2 or due to a value of the offset current OFS2 varying depending on the amount of the existing water vapor or/and the amount of the existing carbon dioxide. This makes it difficult to obtain a hydrocarbon gas concentration accurately based on the Ip2 value.

To reliably obtain the sensitivity characteristics as indicated by the solid line L of FIG. 2, it is more preferable to set the oxygen partial pressure of the first internal space 20 to $10^{-10}$ atm to $10^{-30}$ atm, the oxygen partial pressure of the second internal space 40 to $10^{-5}$ atm to $10^{-15}$ atm, and the oxygen partial pressure on the surface of the measuring electrode 44 to $10^{-0}$ atm to $10^{-10}$ atm.

As described above, in the gas sensor according to this embodiment, the measurement gas, whose oxygen partial pressure has been set to a constantly low value (a value at which the contained inflammable gas does not substantially burn) through the operation of the main pumping cell in the first internal space, is supplied to the second internal space. In the second internal space, the inflammable gases other than hydrocarbon are burned so that the measurement gas contains a hydrocarbon gas alone as the inflammable gas. This measurement gas passes through the third diffusion control part to reach near the surface of the measuring electrode. Hydrocarbon is burned with oxygen on the surface of the measuring electrode. The pump current, which flows through the measuring pumping cell for supplying oxygen in the above-mentioned burning, has a linear relationship with the hydrocarbon concentration in the measurement gas. Based on the above, the hydrocarbon concentration in the measurement gas can be obtained.

According to this embodiment, therefore, even if the measurement element gas contains water vapor or/and carbon dioxide, oxygen generated as a result of the decomposition of water vapor or/and carbon dioxide is pumped out in the first internal space, and hydrogen or/and carbon monoxide generated as a result of the above-mentioned decomposition is burned in the second internal space. At a point of time when the measurement gas reaches the surface of the measuring electrode, thus, only a hydrocarbon gas is included as the inflammable gas components, which allows the hydrocarbon gas concentration to be obtained accurately without being affected by water vapor.

Second Embodiment

Figure 3:
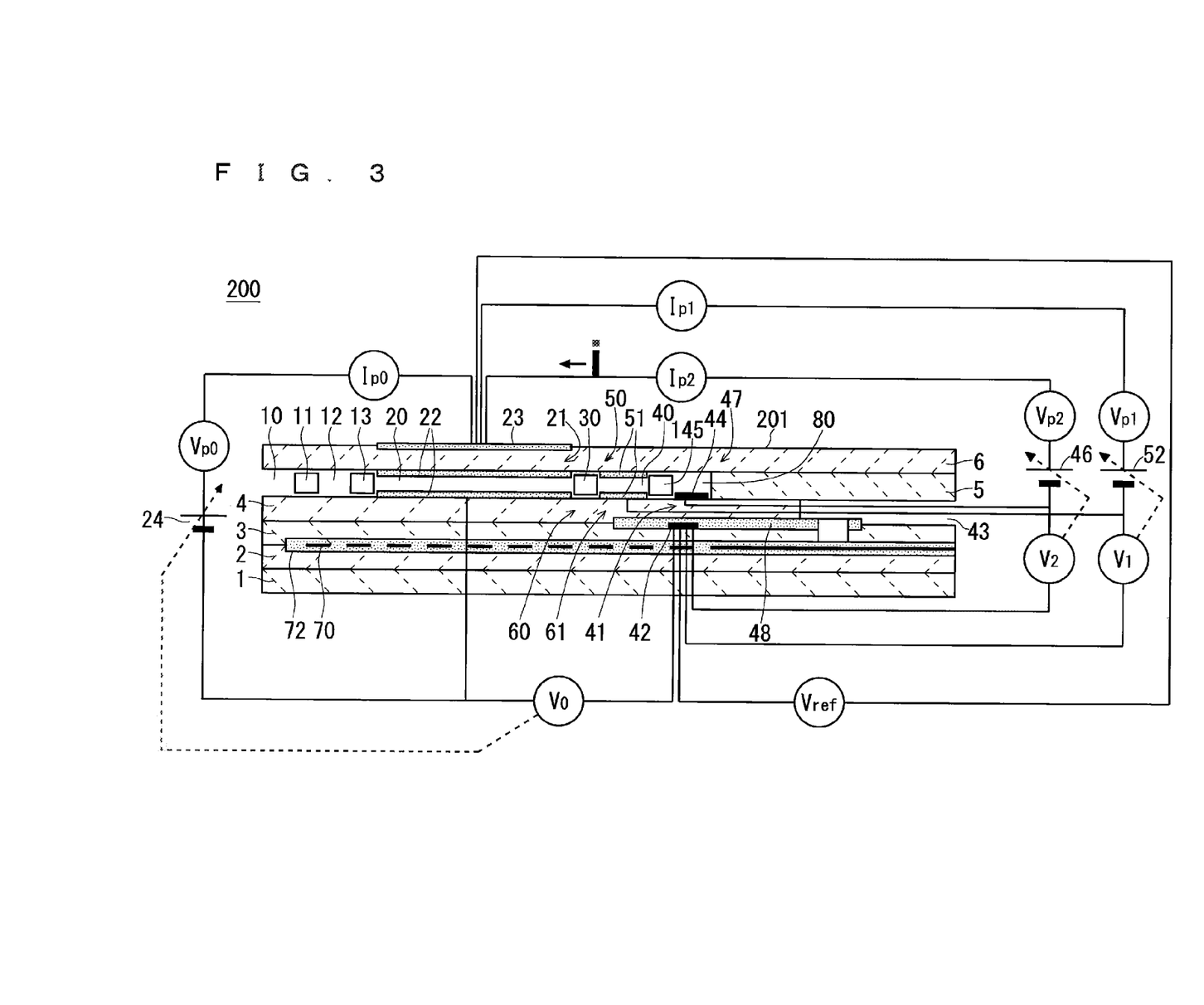
FIG. 3 is a cross-sectional view schematically showing the structure of a gas sensor 200 according to a second embodiment.

FIG. 3 is a cross-sectional view schematically showing the structure of a gas sensor 200 according to a second embodiment of the present invention. In this embodiment, the components included in the gas sensor 200 same as those of the gas sensor 100 according to the first embodiment will be denoted by the same references as those of the first embodiment, which will not be described here.

The sensor element 101 of the gas sensor 100 according to the first embodiment has two internal spaces, namely, the first internal space 20 and the second internal space 40, whereas a sensor element 201 included in the gas sensor 200 according to this embodiment has a third internal space 80 in addition to those two internal spaces. In this embodiment, a part extending from the gas inlet 10 to the third internal space 80 is referred to as a gas distribution part as well.

The third internal space 80 is an interior space provided by hollowing out the spacer layer 5, similarly to the gas inlet 10, the buffer space 12, the first internal space 20, and the second internal space 40. In other words, similarly to the buffer space 12, the first internal space 20, and the second internal space 40, the third internal space 80 is provided, with its upper portion defined by the lower surface of the second solid electrolyte layer 6, its lower portion defined by the upper surface of the first solid electrolyte layer 4, and its side portion defined by the side surface of the spacer layer 5.

The second internal space 40 is provided with only the auxiliary pump electrode 51, and the measuring electrode 44, which is provided in the second internal space 40 in the sensor element 101, is provided in the third internal space 80. The measuring electrode 44 is provided with its surface exposed in the third internal space 80.

Provided between the second internal space 40 and the third internal space 80 is a third diffusion control part 145 as two horizontally long slits (which are openings longitudinally extending to be vertical to the sheet of FIG. 3), similarly to the first diffusion control part 11, the second diffusion control part 30, and the fourth diffusion control part 13. Thus, the measurement gas that has reached the second internal space 40 reaches the measuring electrode 44 provided in the third internal space 80, following the application of a predetermined diffusion resistance by the third diffusion control part 145.

Also in this embodiment, therefore, a measurement gas is introduced in the gas sensor and an inflammable gas is burned, as in the first embodiment, so that the hydrocarbon concentration in the measurement gas can be obtained based on a linear relationship between the pump current flowing through the measuring pumping cell and the hydrocarbon concentration in the measurement gas.

This also allows the gas sensor according to this embodiment to accurately obtain a hydrocarbon gas concentration without being affected by water vapor or/and carbon dioxide even if a measurement gas contains water vapor or/and carbon dioxide.

Modifications

In the embodiment described above, the current flowing between the outside pump electrode 23 and the measuring electrode 44 that constitute the measuring pumping cell 47 is taken as the HC detection current Ip2. Alternatively, the current flowing between the measuring electrode 44 and the reference electrode 42 that constitute the measuring sensor cell 41 may be taken as the HC detection current Ip2 to identify the hydrocarbon gas concentration.

In the embodiment described above, the main pumping cell 21, the auxiliary pumping cell 50, and the measuring pumping cell 47 use the outside pump electrode 23 in common as an external electrode provided on the outer surface of the sensor element 101, which is not necessarily required. As described above, the main pumping cell 21, the auxiliary pumping cell 50, and the measuring pumping cell 47 may individually include a specific external electrode. Or, two external electrodes of the three pumping cells may be shared.

What is claimed is:

1. A hydrocarbon gas sensor that has a sensor element formed of an oxygen-ion conductive solid electrolyte and identifies a concentration of a hydrocarbon gas component of a measurement gas based on a current flowing through said solid electrolyte when said hydrocarbon gas component is burned, said hydrocarbon gas sensor comprising:
   first diffusion control means in communication with the outside for applying a first diffusion resistance to said measurement gas;
   a first internal space that is in communication with said first diffusion control means, into which said measurement gas is introduced with said first diffusion resistance from said outside;
   second diffusion control means in communication with said first internal space for applying a second diffusion resistance to said measurement gas;
   a second internal space that is in communication with said second diffusion control means, into which the measurement gas is introduced with said second diffusion resistance from said first internal space;
   third diffusion control means for applying a third diffusion resistance to said measurement gas introduced into said second internal space;
   a first electrochemical pumping cell formed of a first internal electrode formed to face said first internal space, a first external electrode formed on an outer surface of said sensor element, and said solid electrolyte located between said first internal electrode and said first external electrode;
   a second electrochemical pumping cell formed of a second internal electrode formed to face said second internal space, a second external electrode formed on the outer surface of said sensor element, and said solid electrolyte located between said second internal electrode and said second external electrode;
   a measuring pumping cell formed of a measuring electrode, a third external electrode, and said solid electrolyte located between said measuring electrode and said third external electrode, said measuring electrode being formed so as to come into contact with said measurement gas to which said third diffusion resistance has been applied, said third external electrode being formed on the outer surface of said sensor element;
   a reference gas space into which a reference gas is introduced; and
   a reference electrode formed to face said reference gas space,
   means for causing said first electrochemical pumping cell to adjust an oxygen partial pressure of said first internal space such that a hydrocarbon gas in said measurement gas is not substantially burned in said first internal space,
   means for causing said second electrochemical pumping cell to adjust an oxygen partial pressure of said second internal space such that non-target inflammable gas components of inflammable gas components existing in said second internal space are selectively burned, said non-target inflammable gas components being inflammable gas components including at least hydrogen or carbon monoxide and excluding said hydrocarbon, and
   means for causing said hydrocarbon gas sensor to burn, on a surface of said measuring electrode, all of said hydrocarbon existing in said measurement gas in contact with said measuring electrode after burning of said non-target inflammable gas components, by supplying oxygen to the surface of said measuring electrode by said measuring pumping cell, to thereby identify the concentration of said hydrocarbon gas component existing in said measurement gas based on the magnitude of a current flowing between said measuring electrode and said third external electrode or between said measuring electrode and said reference electrode.

2. The hydrocarbon gas sensor according to claim 1, wherein
   said first electrochemical pumping cell adjusts the oxygen partial pressure of said first internal space through adjustment of a first voltage to be applied between said first internal electrode and said first external electrode,
   said second electrochemical pumping cell adjusts the oxygen partial pressure of said second internal space through adjustment of a second voltage to be applied between said second internal electrode and said second external electrode, and
   said measuring pumping cell adjusts, through adjustment of a third voltage to be applied between said measuring electrode and said third external electrode, an oxygen partial pressure on the surface of said measuring electrode such that said hydrocarbon existing on said surface of said measuring electrode is all burned.

3. The hydrocarbon gas sensor according to claim 2, further comprising:
   a first oxygen-partial-pressure detection sensor cell that detects the magnitude of said first voltage, said first oxygen-partial-pressure detection sensor cell being formed of said first internal electrode, said reference electrode, and said solid electrolyte located between said first internal electrode and said reference electrode;
   a second oxygen-partial-pressure detection sensor cell that detects the magnitude of said second voltage, said second oxygen-partial-pressure detection sensor cell being formed of said second internal electrode, said reference electrode, and said solid electrolyte located between said second internal electrode and said reference electrode; and
   a measuring sensor cell that detects the magnitude of said third voltage, said measuring sensor cell being formed of said measuring electrode, said reference electrode, and said solid electrolyte located between said measuring electrode and said reference electrode, wherein said first electrochemical pumping cell adjusts the oxygen partial pressure of said first internal space based on a detected value of said first voltage in said first oxygen-partial-pressure detection sensor cell, said second electrochemical pumping cell adjusts the oxygen partial pressure of said second internal space based on a detected value of said second voltage in said second oxygen-partial-pressure detection sensor cell, and said measuring pumping cell adjusts the oxygen partial pressure on the surface of said measuring electrode based on a detected value of said third voltage in said measuring sensor cell.

4. The hydrocarbon gas sensor according to claim 1, wherein the concentration of said hydrocarbon gas component is identified while said first electrochemical pumping cell, said second electrochemical pumping cell, and said measuring pumping cell adjust the oxygen partial pressure of said first internal space, the oxygen partial pressure of said second internal space, and the oxygen partial pressure on the surface of said measuring electrode, respectively, so as to satisfy such a relationship that the oxygen partial pressure of said second internal space is larger than the oxygen partial pressure of said first internal space, and the oxygen partial pressure on the surface of said measuring electrode is larger than the oxygen partial pressure of said second internal space.

5. The hydrocarbon gas sensor according to claim 4, wherein the concentration of said hydrocarbon gas component is identified while said first electrochemical pumping cell adjusts the oxygen partial pressure of said first internal space to a value within a range of $10^{-10}$ atm to $10^{-30}$ atm, said second electrochemical pumping cell adjusts the oxygen partial pressure of said second internal space to a value within a range of $10^{-5}$ atm to $10^{-15}$ atm, and said measuring pumping cell adjusts the oxygen partial pressure on the surface of said measuring electrode to a value within a range of $10^{-0}$ atm to $10^{-10}$ atm.

6. The hydrocarbon gas sensor according to claim 4, wherein a target oxygen partial pressure in said first internal space is made smaller as the oxygen partial pressure in said measurement gas becomes larger.

7. The hydrocarbon gas sensor according to claim 1, wherein said measuring electrode is formed on a surface of said second internal space, and said third diffusion control means is a porous layer covering the surface of said measuring electrode.

8. The hydrocarbon gas sensor according to claim 1, in which said third diffusion control means is in communication with said second internal space, said hydrocarbon gas sensor further comprising a third internal space that is in communication with said third diffusion control means, wherein said measuring electrode is formed on a surface of said third internal space.

9. The hydrocarbon gas sensor according to claim 1, wherein at least two of said first external electrode, said second external electrode, and said third external electrode are shared.

10. The hydrocarbon gas sensor according to claim 2, wherein the concentration of said hydrocarbon gas component is identified while said first electrochemical pumping cell, said second electrochemical pumping cell, and said measuring pumping cell adjust the oxygen partial pressure of said first internal space, the oxygen partial pressure of said second internal space, and the oxygen partial pressure on the surface of said measuring electrode, respectively, so as to satisfy such a relationship that the oxygen partial pressure of said second internal space is larger than the oxygen partial pressure of said first internal space, and the oxygen partial pressure on the surface of said measuring electrode is larger than the oxygen partial pressure of said second internal space.

11. The hydrocarbon gas sensor according to claim 3, wherein the concentration of said hydrocarbon gas component is identified while said first electrochemical pumping cell, said second electrochemical pumping cell, and said measuring pumping cell adjust the oxygen partial pressure of said first internal space, the oxygen partial pressure of said second internal space, and the oxygen partial pressure on the surface of said measuring electrode, respectively, so as to satisfy such a relationship that the oxygen partial pressure of said second internal space is larger than the oxygen partial pressure of said first internal space, and the oxygen partial pressure on the surface of said measuring electrode is larger than the oxygen partial pressure of said second internal space.

12. The hydrocarbon gas sensor according to claim 2, wherein said measuring electrode is formed on a surface of said second internal space, and said third diffusion control means is a porous layer covering the surface of said measuring electrode.

13. The hydrocarbon gas sensor according to claim 3, wherein said measuring electrode is formed on a surface of said second internal space, and said third diffusion control means is a porous layer covering the surface of said measuring electrode.

14. The hydrocarbon gas sensor according to claim 4, wherein said measuring electrode is formed on a surface of said second internal space, and said third diffusion control means is a porous layer covering the surface of said measuring electrode.

15. The hydrocarbon gas sensor according to claim 11, wherein said measuring electrode is formed on a surface of said second internal space, and said third diffusion control means is a porous layer covering the surface of said measuring electrode.

16. The hydrocarbon gas sensor according to claim 2, in which said third diffusion control means is in communication with said second internal space, said hydrocarbon gas sensor further comprising a third internal space that is in communication with said third diffusion control means, wherein said measuring electrode is formed on a surface of said third internal space.

17. The hydrocarbon gas sensor according to claim 3, in which said third diffusion control means is in communication with said second internal space, said hydrocarbon gas sensor further comprising a third internal space that is in communication with said third diffusion control means, wherein said measuring electrode is formed on a surface of said third internal space.

18. The hydrocarbon gas sensor according to claim 4, in which said third diffusion control means is in communication with said second internal space, said hydrocarbon gas sensor further comprising a third internal space that is in communication with said third diffusion control means, wherein said measuring electrode is formed on a surface of said third internal space.

19. The hydrocarbon gas sensor according to claim 11, in which said third diffusion control means is in communication with said second internal space, said hydrocarbon gas sensor further comprising a third internal space that is in communication with said third diffusion control means, wherein said measuring electrode is formed on a surface of said third internal space.

* * * * *